(12) United States Patent
Glaser-Seidnitzer et al.

(10) Patent No.: US 8,595,653 B2
(45) Date of Patent: Nov. 26, 2013

(54) METHOD AND USER INTERFACE FOR THE GRAPHICAL PRESENTATION OF MEDICAL DATA

(75) Inventors: Karlheinz Glaser-Seidnitzer, Fuerth (DE); Johannes Kling, Zurich (CH)

(73) Assignee: Siemens Aktiengesellschaft, Munich (DE)

( * ) Notice: Subject to any disclaimer, the term of this patent is extended or adjusted under 35 U.S.C. 154(b) by 727 days.

(21) Appl. No.: 12/420,188

(22) Filed: Apr. 8, 2009

(65) Prior Publication Data

US 2009/0271738 A1  Oct. 29, 2009

(30) Foreign Application Priority Data

Apr. 8, 2008 (DE) .......................... 10 2008 017 846

(51) Int. Cl.
*G06F 3/048* (2013.01)

(52) U.S. Cl.
USPC ........................................................ 715/862

(58) Field of Classification Search
USPC ........................................................ 715/862
See application file for complete search history.

(56) References Cited

U.S. PATENT DOCUMENTS

| | | | | |
|---|---|---|---|---|
| 6,073,036 A | * | 6/2000 | Heikkinen et al. | 455/550.1 |
| 7,058,901 B1 | * | 6/2006 | Hafey et al. | 715/792 |
| 7,434,177 B1 | * | 10/2008 | Ording et al. | 715/862 |
| 7,916,157 B1 | * | 3/2011 | Kelley et al. | 345/660 |
| 2002/0171690 A1 | * | 11/2002 | Fox et al. | 345/862 |
| 2002/0186241 A1 | * | 12/2002 | Kohda et al. | 345/744 |
| 2003/0007017 A1 | * | 1/2003 | Laffey et al. | 345/862 |
| 2005/0047629 A1 | * | 3/2005 | Farrell et al. | 382/117 |
| 2005/0197567 A1 | * | 9/2005 | Qian et al. | 600/425 |
| 2006/0150215 A1 | * | 7/2006 | Wroblewski | 725/47 |
| 2007/0040800 A1 | * | 2/2007 | Forlines et al. | 345/158 |
| 2007/0064984 A1 | | 3/2007 | Vassa et al. | |
| 2007/0162159 A1 | * | 7/2007 | Ladenburger | 700/17 |
| 2007/0209025 A1 | * | 9/2007 | Jing et al. | 715/968 |

(Continued)

FOREIGN PATENT DOCUMENTS

DE  101 58 226 A1  5/2003

OTHER PUBLICATIONS

Leung et al., A Review and Taxonomy of Distortion-Oriented Presentation Techniques, ACM Transactions on Computer-Human Interaction, vol. 1, No. 2, Jun. 1994, pp. 126-160.*

(Continued)

*Primary Examiner* — Matt Kim
*Assistant Examiner* — Ryan Barrett
(74) *Attorney, Agent, or Firm* — Schiff Hardin LLP

(57) ABSTRACT

In a method and a device for the implementation of a medical examination via a user interface of at least one imaging device determination and input of a group of measurement parameters take place via an input device of the user interface. Spatially resolved image information are generated with the at least one imaging device depending on the group of measurement parameters. The image information is stored on a storage medium. The image information is presented as data symbols on a screen of the user interface. Multiple data symbols are presented in a predetermined arrangement on the screen for a medical assessment. An interest value is generated for each of the multiple data symbols with enlarged or reduced presentation of data symbols with higher interest value occurring relative to adjacent data symbols with lower interest value, such that the arrangement of the data symbols with lower interest value in n columns and m rows and at their respective size is maintained.

9 Claims, 4 Drawing Sheets

(56) References Cited

U.S. PATENT DOCUMENTS

2009/0012821 A1* 1/2009 Besson et al. ............... 705/3
2009/0254201 A1* 10/2009 Glaser-Seidnitzer et al. .. 700/17
2009/0254849 A1* 10/2009 Glaser-Seidnitzer et al. 715/771
2009/0276725 A1* 11/2009 Glaser-Seidnitzer et al. 715/771

OTHER PUBLICATIONS

"Exploring Presentation Methods for Tomographic Medical Image Viewing," van der Heyden et al., Artificial Intelligence in Medicine, vol. 22 (2001) pp. 89-109.

* cited by examiner

METHOD AND USER INTERFACE FOR THE GRAPHICAL PRESENTATION OF MEDICAL DATA

BACKGROUND OF THE INVENTION

1. Field of the Invention

The present invention concerns the graphical presentation of medical examination results that were acquired with imaging methods, and in particular a method and a user interface for the implementation of a medical examination.

2. Description of the Prior Art

In the implementation of imaging methods in medical technology (for example magnetic resonance tomography, computed tomography, etc.), large sets (quantities) of data (respectively radiological data sets or data objects) are regularly acquired. Various methods (known as browsers) are known for the necessary consideration, processing and assessment of these acquired data. These browsers for radiological data sets allow the user (radiologist, MRTA) to view the representation of the data sets in detail views or context views.

In known browsers, data objects are presented one-dimensionally in a list or two-dimensionally in a grid, wherein the data objects have a specific size that is variable only via system settings. If the number of data objects to be presented exceeds the space available on the screen, scroll bars are shown with which the user can vertically or horizontally scroll in order to arrive at the desired data object. In these browsers and the methods used therein there is no differentiation between the current user focus (the selected data object) and a current pointer position of an input device and all other data objects. The user thus can easily fail to discern the focus and lose the overview of the presented data sets.

A system and method for dynamic configuration of the presentation on a workstation computer are known from EP 1 764 686 A1. A number of presentations are automatically detected; an application window is generated for each presentation that is independent of the respective other application windows, and a presentation protocol is executed for each application window.

A method to enlarge image objects on a screen is known from DE 101 58 226 A1, which method comprises as steps: determination of a reference object as well as association of an enlargement factor with each pixel dependent on its distance from the reference object.

SUMMARY OF THE INVENTION

An object of the invention is to provide a user interface of a browser for radiological data sets or data objects with which context and detail information of the data (images/series/3D data sets) that are acquired in imaging methods can be clearly presented on a screen.

The basis of the invention is that a pointer position of an input device is evaluated in the browser to present the radiological data sets or, respectively, data objects in order to enable a simultaneous presentation of context information and detail information.

The method according to the invention for the implementation of a medical examination via a user interface of at least one imaging device includes determination and input of a group of measurement parameters via an input device of the user interface, generation of spatially resolved image information with the at least one imaging device dependent on the group of measurement parameters, storage of the image information on a storage medium; and/or presentation of the image information as data symbols on a screen of the user interface. Multiple data symbols are presented in a predetermined arrangement on the screen for a medical assessment. An interest value is generated for each of the multiple data symbols and/or the multiple data symbols are arranged based on the interest value. Data symbols with higher interest value are shown enlarged or shrunk relative to adjacent data symbols with lower interest value; so that the arrangement of the data symbols with lower interest value in n columns and m rows and at their respective size is maintained.

One or more of the following features are advantageously realized in the embodiments of the method:
- data symbols with a high interest value but not a highest interest value are shown shrunk in size, and the data symbol with the highest interest value is shown enlarged,
- the display size of the data symbols with a lower interest value is smaller than the display size of a data symbol with a higher interest value,
- generation of the interest value based on at least one distance between each of the multiple data symbols and the position of a pointer symbol on the screen,
- selection of the data symbol with a higher interest value via manipulation of an input device,
- variation of the interest value of the multiple data symbols with the distance between each of the multiple data symbols and the position of a pointer symbol on the screen,
- representation of the interest value by a border that changes width, color and/or saturation proportional to the interest value,
- representation of the interest value via the transparency of the corresponding data object since the transparency varies proportional to the interest value.

The device according to the invention for the implementation of a medical examination has at least one imaging device to generate spatially resolved image information depending on at least one measurement parameter; a storage medium to store the image information thereupon; and/or a screen for the presentation of the image information as a data symbol thereupon. Multiple data symbols are presented in a predetermined arrangement on the screen for a medical assessment. A control unit is configured to cause generation of an interest value for each of the multiple data symbols; and arrangement of the multiple data symbols based on the interest value.

The device is advantageously provided with an input device to affect the position of a pointer symbol on the screen in order to define an interest value based on at least one distance between each of the multiple data symbols and the position of the pointer symbol on the screen.

An advantage of the invention is that the data symbols are presented in multiple dimensions and can be searched through. This reduces on the one hand the cognitive effort for the user and on the other hand the time costs in the evaluation and finding since all available data objects can be presented simultaneously in an overview, and the selected data object can be shown enlarged, which is why no switching between various views needs to occur.

In other words, a simultaneous presentation of focused and unfocused context information is possible without introducing additional levels or implementing explicit user interactions. The invention solves the problem of the limited available space on the screen via a reduced information content of unfocused objects. It is assumed that such a mode of operation accommodates visually oriented people. The presentation can be adapted without further measures to various questions; the screen space can thereby always be optimally utilized.

The above object also is achieved in accordance with the present invention by a computer-readable medium encoded with programming instructions that, when executed by a computer in which the medium is loaded, because the computer to implement the method according to the invention described above including all embodiments.

DESCRIPTION OF THE PREFERRED EMBODIMENTS

Figure 1:
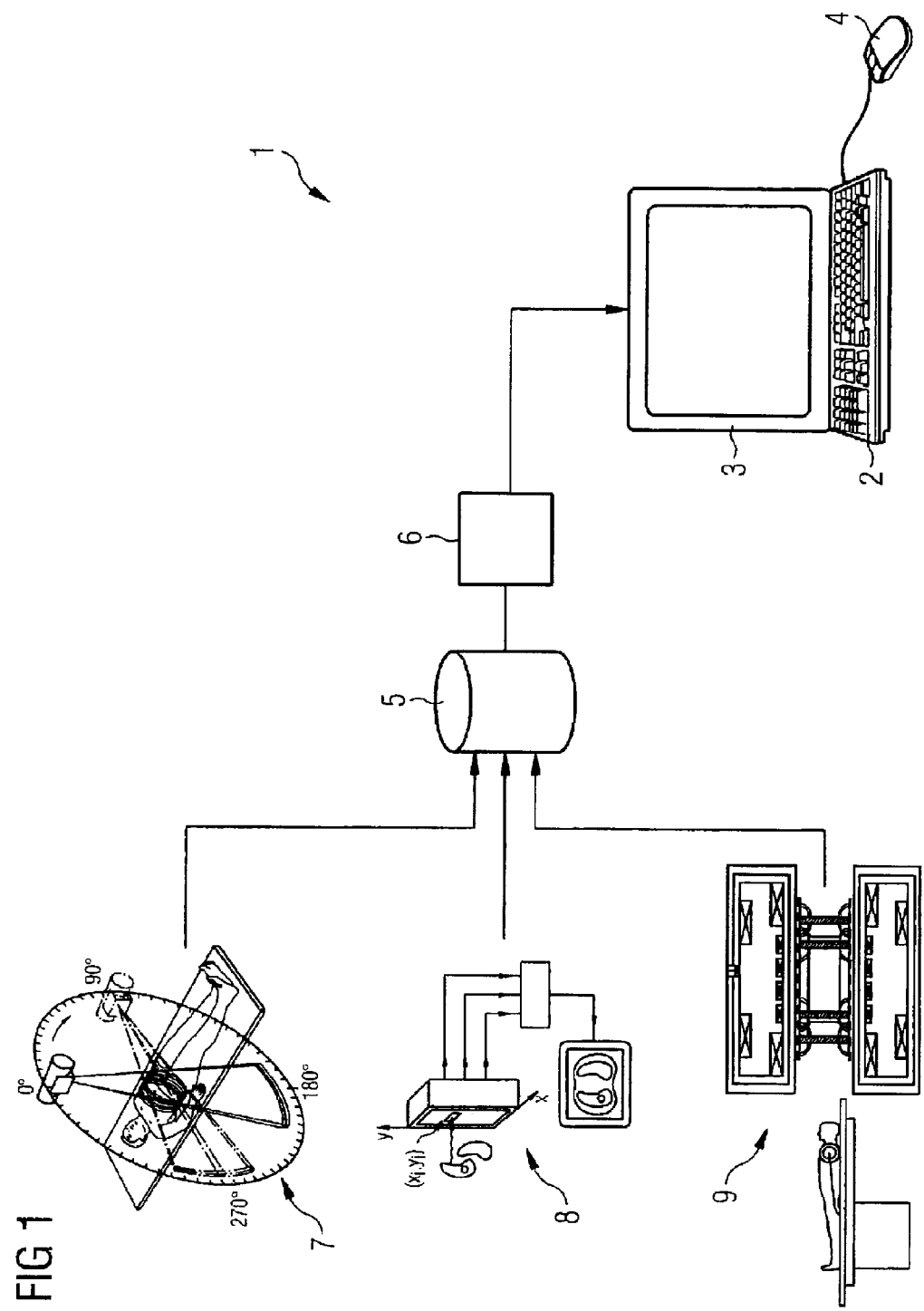
FIG. 1 shows schematically, the design of an embodiment of the user interface according to the invention.

The presentation in the figures is not to scale; identical elements or elements have identical effects are provided with the same reference characters.

The user interface according to the invention utilizes the possibilities of a simultaneous presentation of focused data objects and context information without additional levels or explicit user interactions (such as zoom or pan).

The following terms are used in connection with the Figure description: in the selected presentation, each data object possesses an assumed importance. This assumed importance can be expressed in a value. Given a model of non-equivalent data objects, differences in the importance in this basic value can be shown.

A data object (that is focused on or selected) is designated as a focal point. Moreover, there is an interest value for each object. The interest value defines whether and in what size a data object is visible; the interest value is increased by the assumed importance of the object but is simultaneously reduced with increasing distance from the focal point. If the interest value is less than a predetermined threshold, a predetermined interest value and a predetermined importance for the data object are provided.

The realization of this technical teaching is explained in the following using the figures.

FIG. 1 shows an embodiment of the user interface 1 according to the invention. The user interface 1 comprises an input device for selection by the user of the data objects to be presented. The selected data objects are displayed on a screen 3 of the user interface. The user is assisted in the selection of the data objects to be presented via an electromechanical transducer, for example a computer mouse 4 or a trackball (not shown). Other suitable input devices are, for example, a touchpad, an optical mouse, an eye tracker, a 3D input device, etc.

The display function of the user interface 1 includes retrieval of data or data objects are retrieved from a storage medium 5 and then displayed on the screen 3. The display is thereby controlled by a special control device 6. The presentation of objects on the screen 3 is explained further below using FIGS. 3 through 6.

The data on the storage medium 5 that are displayed on the screen 3 at an arbitrary point in time were acquired with one of three imaging methods and exist as the result of a computed tomography (CT) acquisition 7, or as a result of a positron emission tomography (PET) acquisition 8, or as a result of a magnetic resonance (MR) acquisition 9. Two methods can thereby also be combined with one another, for example PET and CT into PET-CT.

The data from one or more of the imaging methods 7, 8, 9 indicated in FIG. 1 are displayed on the screen 3. The display depends on preset display parameters. These display parameters can in principle be selected independently; their number is also not predetermined in advance.

Figure 2:
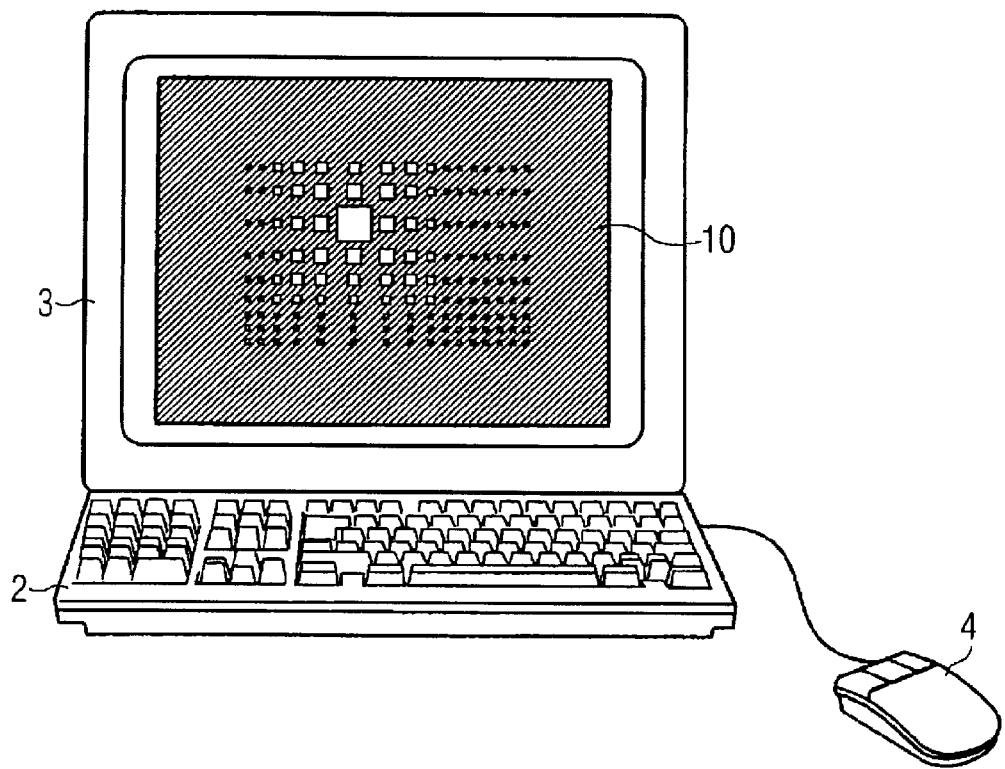
FIG. 2 shows schematically, an example of a display on the user interface according to the invention.

A first example for the display of data objects that are stored on the storage medium 5 is shown in FIG. 2. Multiple data objects 10 are presented in a predetermined arrangement. The predetermined arrangement can be a one-dimensional list (1×m), a two-dimensional grid (n×m) or a three-dimensional coordinate system (n×m×o). These data objects can have been generated with one or more of the imaging methods 7, 8, 9 indicated in FIG. 1. If the data objects have been generated with a single one of the indicated imaging methods 7, 8, 9, the data objects can have been generated with differing parameters or the data objects are presented with differing display parameters.

For example, the various display parameters can correspond to the slice planes in one of the aforementioned imaging methods. Different slice planes can thus be presented and compared in a predetermined arrangement. A data object 11 or a region to be focused on can be selected via an input device 4 by means of a pointer symbol 14 that is positioned at a desired point on the screen.

A maximum interest value 12 is assigned to the data object 11 nearest the region indicated by the pointer symbol 14. The nearest data object 11 is therefore at [sic] the selected data object 11. The assigned interest value 11 is subsequently incorporated into the presentation of the selected data object 11. The selected data object can then be shown enlarged due to the interest value 12. The data objects horizontally, vertically and/or diagonally adjacent to the selected data object 11 likewise receive an increased assigned interest value 13. However, this increased interest value is reduced proportional to the distance between the selected data object 10 and the adjacent data object; this means that, the greater the distance between the selected data object 10 and the adjacent data object, the smaller the interest value 13. It follows from this that the adjacent data objects 10 are presented smaller than the selected data object 11 with increasing distance from said selected data object 11. The interest value 12, 13 can also have effects on the distance between the data objects. If the interest value 13 exceeds a predetermined threshold, this threshold is specified as the interest value 13.

The size of the selected data object 11 can also be varied via manipulation of the input device 2 and/or input device 4. The presentation size of the adjacent data objects 10 as well as the additional data objects 10 can thereby be adapted to the presentation size of the selected data object 11. Furthermore, the unselected data objects 10 can be presented with a reduced information content. It is thereby possible to always utilize the entire space available on the screen. A reduction of the information content can ensue by shrinking the additional data objects 10 or by overlapping at least two data objects.

The term "adjacent data objects" in the present specification means all data objects that are located within a predetermined radius around the selected data object 11. This radius can be varied, for example via the input device 2 and/or the input device 4.

If no data object is focused, the same interest value 12, 13 is assigned to all data objects 10, 11, and they are regularly distributed in the presentation across the space available on the screen 3 in the predetermined presentation.

Additional embodiments are explained in the following using FIGS. 3 through 6. As is recognizable from FIGS. 3 through 6, the pointer position 14 does not need to coincide with the center of the focused data object 11. It is sufficient when the pointer position 14 is located in proximity to an unfocused data object 10, which will then be the distance to the pointer position 14 from the selected data object 11.

Figure 3:
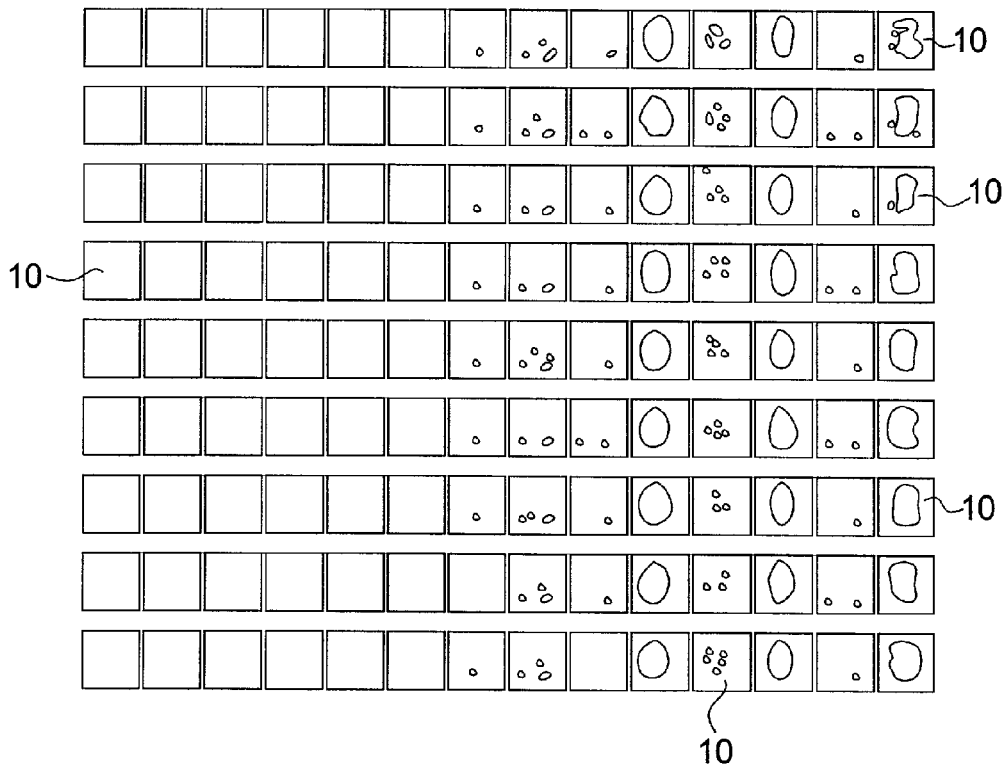
FIG. 3 shows schematically, an example of a starting situation of the presentation according to the invention.

A number of data objects 10 is shown in FIG. 3 that are presented in a predetermined arrangement in the form of n columns×m rows. In FIG. 3, n=14, wherein n is an integer greater than or equal to 1 and m=9, wherein m is an integer greater than or equal to 1. All data objects 10 that, due to their proximity to the focal point, possess an interest value that lies above a preset threshold are shown enlarged. All data objects whose interest value lies below the preset threshold are reduced to a minimum size. Since the pointer position 14 lies outside of the arrangement, all data objects have an interest value that lies below the present threshold and thus are shown in a minimum size.

Figure 4:
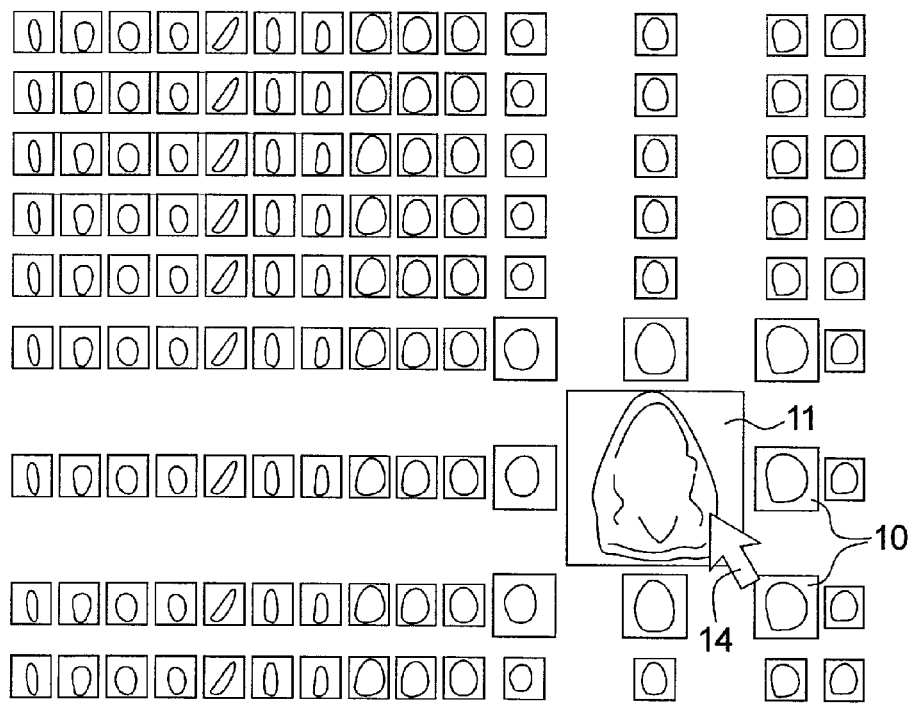
FIGS. 4-6 show additional examples of the presentation according to the invention of patient information on the screen of a user interface according to the invention.

FIG. 4 in turn shows a plurality of data objects similar to FIG. 3. In contrast to FIG. 3, the data object 11 possesses an increased interest value 12 relative to the other data objects 10. The additional data objects 10 possess a reduced interest value 13 and are shown reduced in size. The minimum distance between the data objects 10, 11 thereby remains nearly constant, whereby the enlargement of the data object 11 with an increased interest value 12 leads to a displacement of the data objects 10 with a reduced interest value 13.

Figure 5:
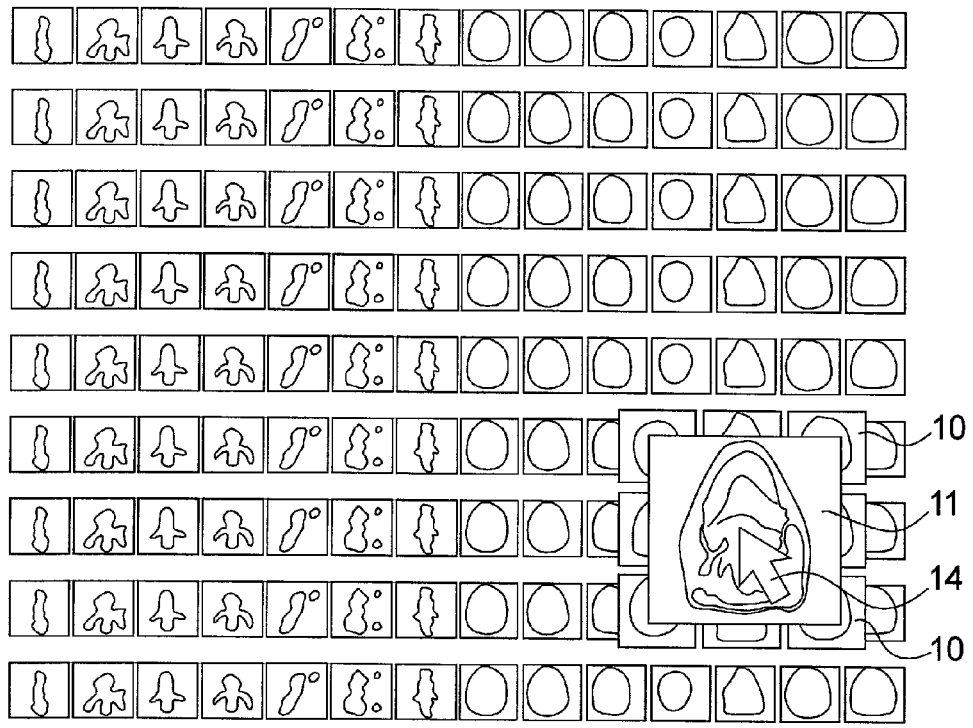

An additional embodiment of the method according to the invention is shown in FIG. 5, wherein the same data objects 10, 11 are shown as in FIGS. 3 and 4. In contrast to FIG. 4, data object, with a degree of interest that does not lie below a preset threshold are not shown reduced in size. No minimum distance between data objects 11 with an increased interest value 12 and data objects 10 with a reduced interest value 13 is maintained either. This leads to the situation that the data object 11 with an increased interest value 12 overlaps data objects 10 with a reduced interest value 13.

Figure 6:
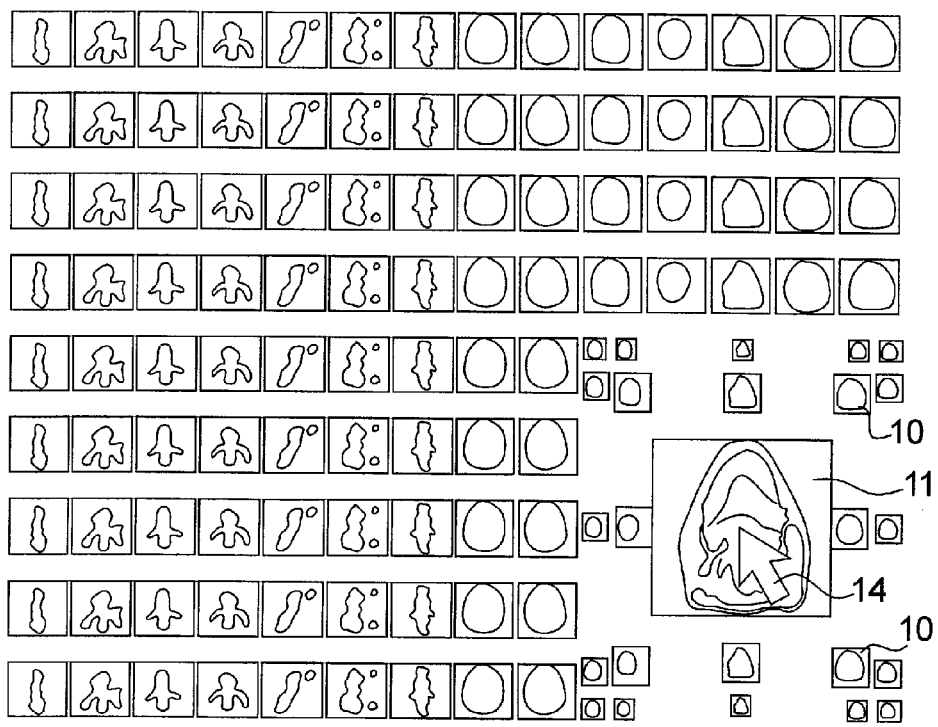

FIG. 6 shows an additional embodiment of the method according to the invention. The same data objects 10, 11 as in FIGS. 3, 4 and 5 are shown in FIG. 6. In contrast to FIG. 5, data objects with an interest value 13 below a predetermined threshold maintain their initial position and initial size. Data objects 10 with an interest value over a predetermined threshold are shown reduced in size, except for the data object 11 which represents the focal point. The degree of the shrinking is dependent on the distance of the data object 10 from the focal value/data object.

A method and a device are specified for the implementation of a medical examination via a user interface of at least one imaging device, operates as follows. Determination and input of a group of measurement parameters takes place via an input device of the user interface. Spatially resolved image information are generated with the at least one imaging device, depending on the group of measurement parameters. The image information is stored on a storage medium. The image information is presented as data symbols on a screen of the user interface. Multiple data symbols are presented in a predetermined arrangement on the screen for a medical assessment. An interest value is generated for each of the multiple data symbols; and arrangement of the multiple data symbols based on the interest value.

The aforementioned embodiments can be implemented as software modules and/or hardware modules in the corresponding function blocks. The present invention is not limited to the aforementioned embodiments, but rather can be applied in other methods and devices for the implementation of a medical examination via a user interface.

We claim as our invention:

1. A method for implementing a medical examination via a user interface of a medical imaging device, comprising the steps of:

determining a group of measurement parameters for implementing a medical examination and entering said group of measurement parameters into of a user interface of a medical image data acquisition device;

with said medical imaging device, acquiring spatially resolved image information dependent on said group of measurement parameters, and storing said spatially resolved image information on a storage medium;

accessing said spatially resolved image information from said storage medium and presenting said spatially resolved image information as a plurality of multi-pixel medical images on a single display screen of the user interface, in an arrangement of n columns and m rows with each multi-pixel medical image having a predetermined size on said single display screen for a medical assessment;

via an indicator device that interacts with said display screen, designating one of said multi-pixel medical images as a selected image;

in said user interface, assigning said selected image a highest interest value and automatically generating respective interest values for each of the multi-pixel medical images, other than said selected image, that are dependent on and below said highest interest value; and presenting all of said plurality of multi-pixel medical images in said arrangement on said single display screen based on said interest values, and presenting only said selected image with the highest interest value at said display screen in an enlarged form larger than said predetermined size, and shrinking other multi-pixel medical images among said plurality of multi-pixel medical images, having a high interest value but not said highest interest value, to a size smaller than said predetermined size.

2. A method as claimed in claim 1 comprising generating said interest value to decrease with a distance between respective ones of the multi-pixel medical images and a position of said selected image on said single display screen.

3. A method as claimed in claim 1 comprising presenting said multi-pixel medical images in an arrangement selected from the group consisting of a one-dimensional list, a two-dimensional grid, and a three-dimensional coordinate system.

4. A device for implementing a medical examination via a user interface of a medical imaging device, comprising:

a processor;

an input unit configured to allow entry into said processor of a group of measurement parameters for implementing a medical examination with a medical image requisition device operate by said processor;

said processor being configured to operate said medical image acquisition device to acquire spatially resolved image information dependent on said group of measurement parameters;

a storage medium which said spatially resolved image information is stored;

a display having a single display screen;

said processor being configured to access said spatially resolved image information from said storage medium and to present said spatially resolved image information as a plurality of multi-pixel medical images on said single display screen, in an arrangement of n columns and m rows with each multi-pixel medical image having a predetermined size on said single display screen;

said input unit comprising a user-operate indicator and said processor being configured to allow user interaction via said indicator with said display screen to designate one of said multi-pixel medical images as a selected image;

said processor being configured to assign said selected image as highest interest value and to automatically generate respective interest values for each of the multi-pixel medical images other than said selected image that are dependent on and below said highest interest value, present only said data image with the highest interest value at said display screen in an enlarged form larger than said predetermined size, and to shrink other multi-pixel medical images among said plurality of multi-pixel medical images, having a high interest value but not said highest interest value, to a size smaller than said predetermined size.

5. A device as claimed in claim 4 wherein said processor is configured to generate said interest value based on a distance between the respective multi-pixel medical images and a position of said selected image on said single display screen.

6. A non-transitory, computer-readable storage medium encoded with programming instructions for implementing a medical examination via a computerized user interface of a medical imaging device, said programming instructions causing said user interface to:

receive a group of measurement parameters for implementing a medical examination with a medical image acquisition device in communication with said user interface;

operate said medical image acquisition device to acquire spatially resolved image information dependent on said group of measurement parameters, and store said spatially resolved image information on a storage medium;

access said spatially resolved image information from said storage medium and present said spatially resolved image information as a plurality of multi-pixel medical images on a single display screen of the user interface, in an arrangement of n columns and m rows with each multi-pixel medical image having a predetermined size on said single display screen for a medical assessment;

interact with a user-manipulated indicator on said single display screen to select one of said multi-pixel medical images in said presentation as a selected image;

assign said selected image as highest interest value and to automatically generate respective interest values for each of the multi-pixel medical images other than said selected image that are dependent on and below said highest interest value; and present said multi-pixel medical images in said arrangement on said single display screen based on said interest values, with only said selected image with the highest interest value presented at said display screen in an enlarged form larger than said predetermined size, and with other multi-pixel images among said plurality of multi-pixel medical images, having a high interest value but not said highest interest value, shrunk to a size smaller than said predetermined size.

7. A method as claimed in claim 1 comprising presenting said selected image having said highest interest value in said enlarged form superimposed over said other multi-pixel medical images having said size smaller than said predetermined size.

8. A device as claimed in claim 4 wherein said processor is configured to present said selected image having said highest interest value in said enlarged form superimposed over other multi-pixel medical images having said size smaller than said predetermined size.

9. A non-transitory, computer-readable storage medium as claimed in claim 6 wherein said programming instructions cause said user interface to present said selected image having said highest interest value in said enlarged firm superimposed over other multi-pixel medical images having said size smaller than said predetermined size.

\* \* \* \* \*